United States Patent
Turto et al.

Patent Number: 5,916,186
Date of Patent: Jun. 29, 1999

[54] HAND SPLINT APPARATUS

[75] Inventors: Craig H. Turto; William J. Hancock; Peer Lindemann, all of Palm Harbor, Fla.

[73] Assignee: Medassist OP, Inc., Palm Harbor, Fla.

[21] Appl. No.: 08/882,843

[22] Filed: Jun. 26, 1997

[51] Int. Cl.[6] .................................................. A61F 5/00
[52] U.S. Cl. .............................. 602/20; 602/21; 602/12
[58] Field of Search ..................... 602/5, 6, 12, 20–22, 602/60, 62, 64; 128/878, 879; 24/665, 672

[56] References Cited

U.S. PATENT DOCUMENTS

| | | | |
|---|---|---|---|
| D. 244,152 | 4/1977 | Kvittingen | D24/64 |
| 1,328,598 | 1/1920 | Schilling . | |
| 2,312,523 | 3/1943 | Corbett | 128/85 |
| 3,256,880 | 6/1966 | Caypinar | 128/133 |
| 3,526,006 | 9/1970 | Beardmore | 3/12 |
| 3,745,997 | 7/1973 | Gledhill | 128/88 |
| 3,913,570 | 10/1975 | Madden et al. | 602/5 |
| 3,937,215 | 2/1976 | Bartholme | 128/26 |
| 3,938,509 | 2/1976 | Barber | 602/21 |
| 3,942,522 | 3/1976 | Kinnier Wilson | 602/6 |
| 4,274,399 | 6/1981 | Mummert | 128/26 |
| 4,522,197 | 6/1985 | Hasegawa | 128/26 |
| 4,596,240 | 6/1986 | Takahashi et al. | 128/26 |
| 4,619,250 | 10/1986 | Hasegawa | 128/26 |
| 4,671,258 | 6/1987 | Barthlome | 128/26 |
| 4,673,070 | 6/1987 | Ambal | 24/665 X |
| 4,677,971 | 7/1987 | Lindemann | 128/87 |
| 4,768,502 | 9/1988 | Lee | 128/87 |
| 4,907,574 | 3/1990 | Hollerbach | 128/64 |
| 4,928,677 | 5/1990 | Barber | 602/21 |
| 4,977,890 | 12/1990 | Mann | 128/77 |
| 4,993,422 | 2/1991 | Hon et al. | 128/672 |
| 5,020,515 | 6/1991 | Mann et al. | 128/26 |
| 5,056,504 | 10/1991 | Mann | 128/26 |
| 5,152,739 | 10/1992 | Grob | 602/5 |
| 5,152,740 | 10/1992 | Harkensee et al. | 602/13 |
| 5,358,471 | 10/1994 | Klotz | 602/21 |
| 5,472,409 | 12/1995 | Hoy | 602/20 X |
| 5,611,735 | 3/1997 | Jackson | 473/60 |

*Primary Examiner*—Richard J. Apley
*Assistant Examiner*—Denise Pothier
*Attorney, Agent, or Firm*—Carlton Fields et al.

[57] ABSTRACT

The hand splint apparatus of the present invention is directed to a hand splint apparatus and method of attaching a hand splint apparatus to a patient's forearm that includes a forearm support, an elongated and inelastically deformable connector having an axis extending between a first and second end thereof, with the connector first end attached to the forearm support and with the connector second end attached to a hand piece proximal to a first end of the hand piece, such that the connector is adjustable in a plurality of directions transverse to the connector axis for orienting the hand piece to a desired position with respect to the forearm support.

24 Claims, 6 Drawing Sheets

HAND SPLINT APPARATUS

BACKGROUND OF THE INVENTION

The present invention relates generally to a hand splint and, more particularly, to a therapeutic hand splint support adaptable to a specific patient for positioning the patient's wrist, hand and/or fingers at a desired position.

Individuals who experience numerous medical conditions, such as neurological diseases or impairments, strokes, arthritis, orthopedic injuries and muscular diseases, often suffer from flexion, extension, or contractures to the wrist, hand and fingers. These conditions may result in a loss of range of motion or may require immobilization or functional support. Regardless of the amount of the contracture, a common goal is to restore at least a substantial portion of the functionality to the patient's injured hand. In order to accomplish this goal, patients typically undergo physical therapy that includes applying braces and splints particularly developed for alleviating and rehabilitating such physical conditions of the hands, wrists and fingers.

Numerous conventional splints have been developed for use in treating contractures of the wrist and fingers. For example, U.S. Pat No. 4,977,890 discloses a hand splint that includes a forearm support and a wrist rod bendable upwardly and downwardly at a pivot point to position a palmer device at a desired unilateral position. Another patent, U.S. Pat. No. 4,677,971, discloses an adjustable wrist splint having a forearm support attached to a hand support by a ball-and-socket joint that may be locked to a desired position by tightening a series of screws. Yet another somewhat cumbersome approach is disclosed in U.S. Pat. No. 4,768,502, in which a web-like forearm support is attached to a collar that may be adjusted by aligning a pair of holes in the collar with selected pairs of a plurality of holes in the forearm support and locking the collar to the support with screws. Further analysis of these and other prior art readily leads one to the conclusion that such conventional splints and braces either provide a complex apparatus difficult for use by a therapist or otherwise fail to accommodate the various amounts of radial and ulnar deviation that often accompany such contractures. In addition, conventional apparatus that may provide desired adjustability usually requires additional tools or otherwise includes complex adjustment mechanisms for adjusting the splint for a particular patient. Accordingly, there remains a great need for an improved hand splint that is not only relatively simple in construction, but that also provides an effective and manageable therapeutic solution that may be easily applied by a therapist or technician.

SUMMARY OF THE INVENTION

It is an object of the present invention to provide an adjustable hand splint apparatus adaptable to the therapeutic needs of a particular patient. It is another object of the present invention to provide a hand splint apparatus capable of accommodating various contractures to the patient's wrist, hand, or fingers or combinations of those contractures. It is still another object of the present invention to provide a hand splint that is relatively simple to use and adjust by a therapist or technician, and yet relatively inexpensive to manufacture.

In order to accomplish these objects and others that will become apparent to those skilled in the art, the present invention provides an adjustable hand splint apparatus that includes a generally rigid forearm support having a first end, a second end and an axis extending between the first and second ends thereof, an elongated and inelastically deformable connector having a first end, a second end and an axis extending therebetween, with the connector first end attached to the forearm support at a position proximal to the forearm support second end, with the connector second end distal the forearm support, and a hand piece having a first end and a second end, with the connector second end attached to the hand piece at a position proximal to the hand piece first end, with the connector being adjustable in a plurality of directions transverse to the connector axis for orienting the hand piece to a desired position with respect to the forearm support.

BRIEF DESCRIPTION OF THE DRAWINGS

Preferred embodiments of the present invention are illustrated in the drawings in which.

DETAILED DESCRIPTION OF PREFERRED EMBODIMENTS

A preferred embodiment of the present invention is illustrated in FIGS. 1–10, in which similar reference numbers, increased by adding integer multiples of 100, refer to similar parts throughout the various views.

The preferred embodiment of the present invention includes a generally rigid forearm support 12 having a first end 14, a second end 16 and a longitudinal axis 18 extending through the first and second ends 14 and 16, respectively. In the preferred embodiment illustrated in FIGS. 1, 3, 5, and 6, the forearm support 12 is shown to include a generally rigid frame 20, which may be conveniently a wire loop of metal, such as aluminum, stainless steel or other generally rigid material. Preferably, a generally rigid longitudinal support, shown as elongated rib 22, which may suitably be an elongated, thin metal sheet, is attached between the first and second ends of frame 20, suitably by welding or applying an industrial adhesive material or using another conventional fastener. The side portions 24 and 26 of frame 20, which are positioned on generally opposed sides of longitudinal rib 22, may conveniently be bendable to conform the forearm support 12 generally to the shape of the patient's arm. In order to provide further comfort to the patient, the forearm support 12 may also include a foam enclosure 28 surrounding at least a portion of, although suitably the entire, forearm support 12, with a portion of the foam enclosure at a position proximal to the forearm support second end 16 having an opening 27 formed therein. As is best shown in the exploded view of FIG. 6, foam enclosure 28 may include two sheets 29 and 30 of an closed cell foam, such as VOLARA™ manufactured by Voltek Corp. of Lawrence, Mass., that sandwich support 12 and are preferably bonded together by an appropriate adhesive material therebetween. In addition, a plurality of mating fasteners 31A and 31B, 32A and 32B as well as 33A and 33B, which may be conventional hook and loop materials, may be attached to the inner surface of foam sheets 29 and 30 surrounding the forearm support second end 16, as shown in FIG. 6.

Referring to FIGS. 1–5, hand splint 10 also includes a generally elongated and inelastically deformable connector 34 having a first end 36, a second end 38 spaced a predetermined distance apart from first end 36, and an axis 40 extending longitudinally through the connector ends, suitably coaxial, when in use, with axis 18. The connector first end 36 is attached to forearm support 12 at a position proxial to forearm support first end 14. The connector second end 38 extends outwardly from forearm support second end 16 and is attached to a hand piece, generally indicated as element 42, 142, 242, or 342 in the various figures. The connector 34 of the present invention is adjustable in a plurality of directions transverse to the connector axis 40. Preferably, the connector first end 36 is formed of a generally planar member 44 defining a first plane 46, with the connector second end 38 being adjustable with respect to the connector first end planar member 44 in a direction generally transverse to the plane 46, indicated as reference character A in FIG. 1, as well as in a direction generally parallel to the plane 46, indicated as reference character B. The preferred embodiment of the present invention is also angularly adjustable generally about the connector axis 40, such that the connector second end 38 may be angularly adjusted with respect to connector first end 36 about connector axis 40. Accordingly, hand piece 42, 142, 242 or 342 attached to connector second end 38 may be positioned to a desired angle about axis 40 with respect to the forearm support 12. This angular adjustability about axis 40 is indicated as reference character C in FIG. 1. Thus, a therapist or technician may position hand piece 42 at a desired position with respect to forearm support 12 by conveniently displacing the hand piece 42 along directions A and B and rotating it a desired angle C about axis 40, with the connector staying deformed or bent at such desired position without any significant loss of structural rigidity.

Figure 2:
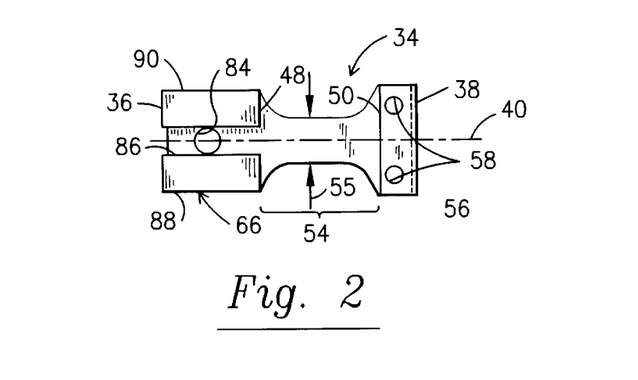
FIG. 2 is a preferred embodiment of an untwisted connector member in accordance with the present invention.
Figure 3:
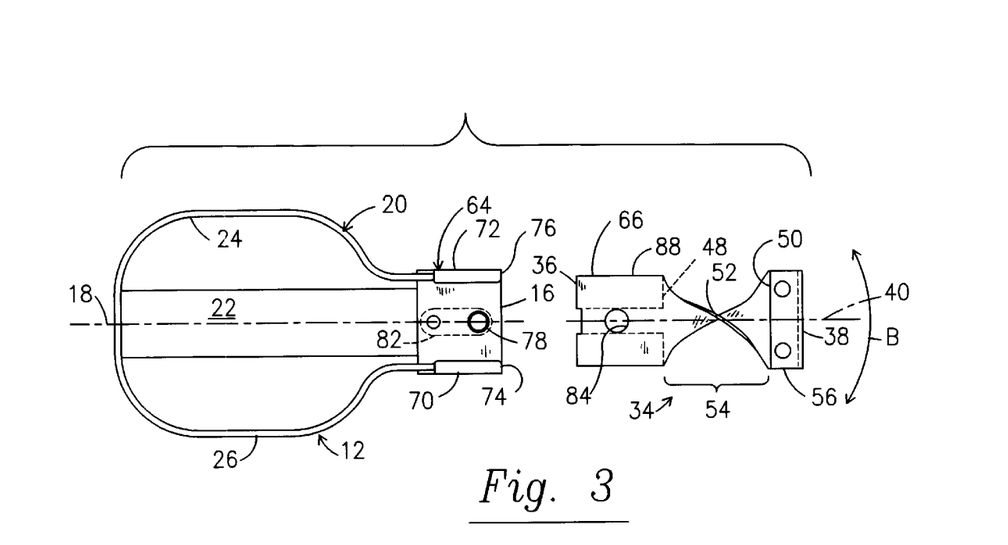
FIG. 3 is an exploded view of a preferred embodiment of a forearm support and a twisted connector member in accordance with the present invention.

A particularly preferred embodiment of connector 34 is illustrated in FIGS. 2 and 3, as an inelastically deformable member having first end 36 and second end 38 with axis 40 extending therebetween, and with the member first end 36 being rotated approximately 180° about the member axis 40 with respect to the member second end 38 to define a twist 52 in the member between member ends 36 and 38, with twist 52 having generally parallel planar end portions 48 and 50, with the portion between these end portions being indicated as 54. It has been found that forming the connector member 34 of a inelastically deformable material, such as aluminum, stainless steel or the like provides sufficient rigidity to a patient and enables a therapist to easily adjust the splint 10 to a desired position according to the patient's injury. Deformable connector 34 suitably requires about 30 to about 50, and preferably about 44, pounds of force to bend the twisted member 34 when connected between the forearm support and the hand piece. In addition, the twist between ends 48 and 50 permits the member second end 38 to be adjusted with respect to member first end 36 in directions A and B, and permits angular rotation of member second end 38 with respect to member first end 36 about axis 40 in direction C. Thus, the twisted connector 34 attached between support 12 and a hand piece, such as 42, 142, 242 or 342, provides for adjustment and readjustment of the hand piece in a multitude of directions, such that it may accommodate substantially any contracture of the hand and wrist.

FIG. 2 illustrates connector 34 prior to forming twist 52 in intermediate portion 54. The portion of connector 34 intermediate first and second twist ends 48 and 50 has a predetermined width, indicated as 55, that is less than the width of end portion 56 intermediate twist end 50 and connector second end 38. This relatively wide end portion 56 attaches to hand piece 42, 142, 242, or 342 in a conventional manner, such as by threaded fasteners, rivets, welding, or other suitable fasteners known in the art. In the preferred embodiment, threaded fasteners or rivets may be inserted through spaced-apart apertures 58 formed through portion 56 to secure connector second end 38 to the respective hand piece 42, 142, 242, or 342. Intermediate portion 54 essentially defines an inelastically deformable joint for orienting the hand piece 42 with respect to forearm support 12 to any one of numerous fixed positions along directions generally transverse to connector axis 40 as well as angularly thereabout, suitably identified as in directions A, B and C.

As stated above, the hand splint 10 of the present invention also includes a hand piece, which may include any of a number of functional hand pieces, such as 42, 142, 242, and 342, illustrated in FIGS. 1 and 4–10. The particular hand piece selected for a given patient will generally depend upon several factors, including the severity of the contracture as well as the medical condition that brought about the contracture.

Figure 1:
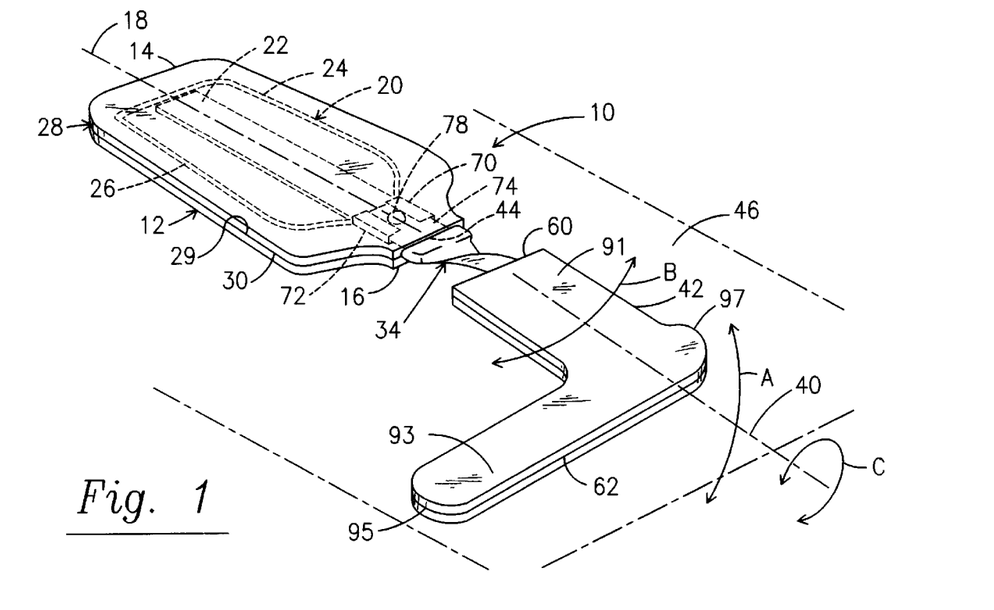
FIG. 1 is a perspective view of a preferred embodiment of a hand splint apparatus in accordance with the present invention, illustrating an L-shaped hand piece.

One type of hand piece is the generally L-shaped hand piece 42, shown in FIGS. 1, 4, 6 and 7. In general, the L-shaped support 42, which may suitably be formed of a sheet of a generally rigid material, such as aluminum, stainless steel or a rigid thermoplastic material, has a first end 60, a second end 62 and a first planar portion 91 extending therebetween and having a predetermined width. Connector second end 38 is attached to the hand piece first end 60 to provide for the adjustability of hand piece 42 with respect to forearm support 12. At a position proximal second end 62, support 42 also includes a second elongated planar portion 93 extending generally coplanar with first planar portion 91 and extending generally normal to axis 40 to define the L-shaped member 42 shown in FIGS. 1, 6 and 7. Second planar portion 93 has first and second ends 95 and 97, with first end 95 extending a first predetermined distance from first planar portion 91 and terminating in curved end 95. A second end of planar portion 93 may extend a shorter distance from portion 91, preferably forming the relatively short arcuate end 97, as shown in FIGS. 1 and 6. L-shaped hand piece support 42 is preferably formed of a thin sheet of a substantially rigid material, such as stainless steel, aluminum or a suitably rigid thermoplastic material, suitably KYDEX™, which is manufactured by Kleerdex Co. of Bloomsburg, Pa., and is covered with a foam material, such as the closed cell foam material VOLARA. L-shaped support 42, when used in connection with the forearm support 12, generally allows the hand to bend generally around second portion 93 but restrains the wrist from flexing. In addition, the L-shaped support 42 may be used with a cylindrical roll having a predetermined radius that slides over end portion 93 to increase the size thereof and to space the fingers a desired distance apart from the patient's palmer region, according to the size of the cylindrical roll.

Figure 4:
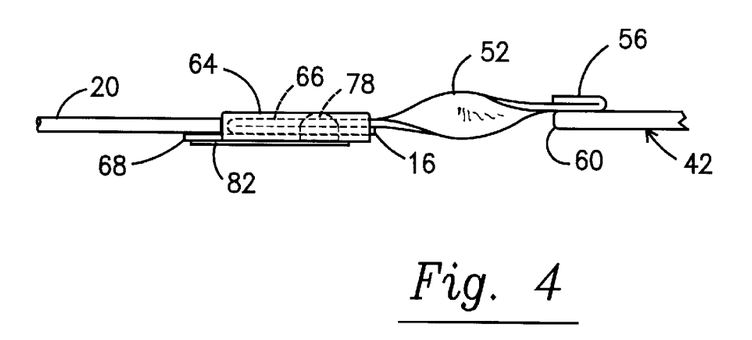
FIG. 4 is a partial side elevation of a preferred embodiment of the hand splint of FIG. 1.

In the preferred embodiment illustrated in FIGS. 1, 4 and 6, the hand piece 42 is removably attached to forearm support 12 by a detachable connector 34. It will be understood and appreciated by those skilled in the art that the present invention operates extremely well without the additional modularity, and that the additional functionality of the detachable connector further enhances the utility of the present invention. Hand splint 10 includes a detachable coupling or connector removably attached between the hand piece first end 60 and the forearm support second end 16 for selectively detaching the desired hand piece 42 from forearm support 12 as well as for selectively attaching another of the hand pieces 142, 242 or 342 thereto, as shown in FIG. 6.

Unless indicated otherwise, the following description relating to a preferred embodiment of the detachable coupling is equally applicable to other hand pieces, which may include hand pieces 142, 242, and 342, illustrated in FIGS. 6 and 7–10. Preferably, as shown in FIGS. 1–4, the detachable coupling includes mating first and second parts 64 and 66, with one of the coupling parts 64 being secured to the forearm support second end 16 and the other coupling part 66 secured to the hand piece proximal first end 60. In this embodiment removable coupling portion 64 is shown as a female member, which may be in the form of a receiving platform or a sleeve 68 having a pair of generally opposed and spaced apart side edges 70 and 72. Preferably, side edges 70 and 72 include a respective pair of generally opposed, spaced apart and generally parallel channels 74 and 76 formed therein generally parallel to forearm support axis 18. Channels 74 and 76 are dimensioned and configured for receiving removable coupling portion 66. Receiving platform 68 is attached to forearm support second end 16, suitably by welding or applying an appropriate adhesive material between edges 70 and 72 and annular loop side portions 24 and 26 as well as between support rib 68 and platform 68 proximal forearm support second end 16, such that the planar portion of member 68 is positioned substantially parallel to the longitudinal support rib 22. The preferred embodiment of connector portion 64 also includes a detent 78 positioned proximal forearm support second end 16 intermediate side edges 70 and 72. Preferably, detent 78 is formed of a button or pin biased to move generally normal to receiving platform 68 through an aperture 80 formed through the platform 68, suitably along axis 18. Detent 78 is attached to receiving platform 68 by a biasing element 82 for biasing detent 78 through aperture 80, which element 82 may conveniently be a resilient sheet secured to platform 68 at a position generally along axis 18 spaced a predetermined distance apart from aperture 80.

Figure 3A:
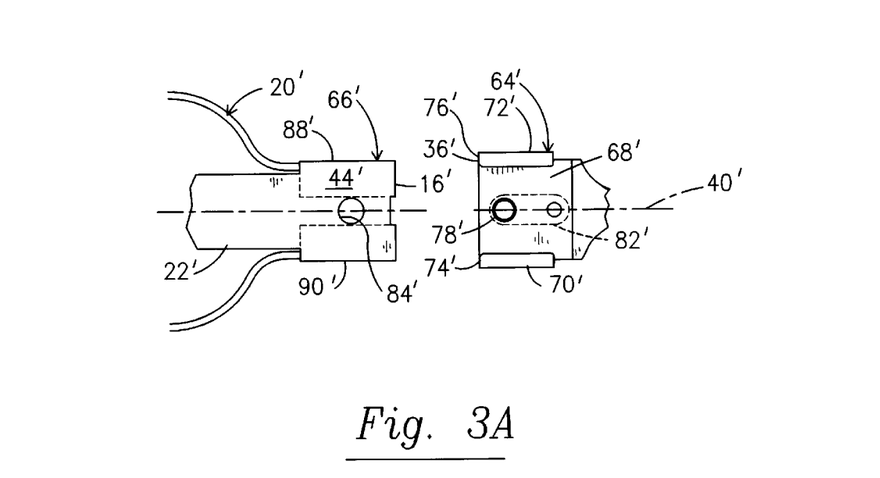
FIG. 3A is a fragmentary exploded view of the forearm support and connector of FIG. 3 in which the male and female coupling parts have been switched.

The connector first end comprises coupling second part 66, which is insertable between channels 74 and 76 and further includes a receptacle 84, suitably in the form of an aperture, an indentation, a notch, a slot or other structure capable of receiving detent 78, for removably attaching connector first end 36 to forearm support 12. Coupling second part 66 that attaches to coupling first part 64 is preferably formed of a generally planar member, such as a sheet or a generally flat arm, having a pair of side edges 88 and 90 spaced apart a predetermined distance according to the distance between channels 74 and 76, with receptacle 84 formed intermediate side edges 88 and 90 at a position for receiving detent 78 when inserted into and received by coupling 46. In order to facilitate the reception of detent 78 within receptacle 84, the surface of connector portion 66 that engages receiving platform 68 of the forearm support further includes a channel 86 having a predetermined depth and a width at least equal to the diameter of detent 78, which channel extends generally along connector axis 40 and intersects receptacle 84. Channel 86 may conveniently be formed by securing a pair of elongated, spaced apart and substantially parallel plates to one side of the planar member of coupling 64 on opposed sides of receptacle 84 and parallel to axis 40, or by folding over the outer edges of the coupling second part 66. Thus, as coupling 64 is inserted into channels 74 and 76, a portion of detent 78 may extend within channel 86 until biasing element 82 urges detent 78 to engage receptacle 84, thereby removably locking coupling 64 with coupling 66. Obviously the female coupling first part 64 and the male coupling second part 66 could be interchanged in their positions if desired, as shown in FIG. 3A, with similar parts being indicated by adding a prime symbol.

As stated above, the present invention may comprise numerous interchangeable hand pieces in order to control the relationship of a patient's hand and fingers according to a particular therapeutic goal. With the preferred embodiment of the present invention a single forearm support 12 may be used in combination with different hand pieces as part of a therapeutic regimen. While numerous such hand pieces may be used with the present invention, four particularly preferred embodiments are described herein, the L-shaped support 42 having been described above.

Figures 9, 10:
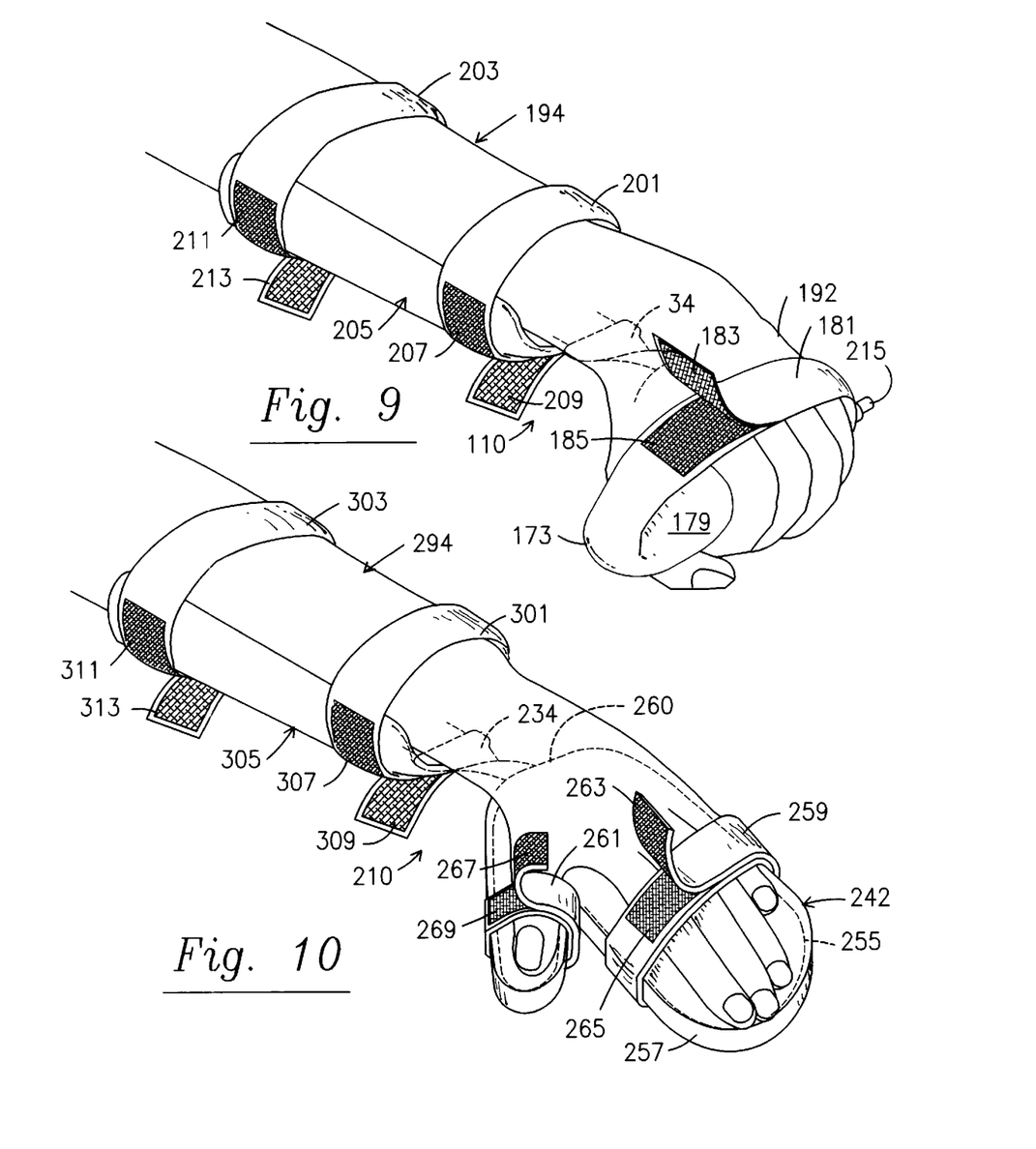
FIG. 9 is a preferred embodiment of a hand splint apparatus having an inflatable bladder, illustrating a preferred manner of attachment to a patient's hand and forearm.
FIG. 10 is a preferred embodiment of a hand splint apparatus having a resting platform, illustrating a preferred manner of attachment to a patient's hand and forearm.

A hand piece comprising an inflatable bladder is illustrated in FIGS. 6 and 9, in which similar reference numbers correspond to similar parts of the removable connector 34 and hand piece 42 described above by adding 100. Hand piece 142 includes a generally rigid planar mount 159, which may be formed of a generally rigid material, such as stainless steel, aluminum, a generally rigid thermoplastic material, suitably KYDEX, or other conventional rigid materials. The planar mount 159 has a first end 160, which may be attached to connector second end 138 by a pair of fasteners 165 and 167, which may conveniently be threaded fasteners, rivets, a weld or an appropriate adhesive material. Planar mount 159 also has two surfaces, one of which surfaces 169 is attached to a generally cylindrical, elongated inflatable bladder 171, suitably with an appropriate adhesive material. It will, of course, be understood and appreciated that various bladder configurations may be used in connection with the splint of the present invention. The particularly preferred embodiment illustrated in FIG. 6 is directed to a generally cylindrical bladder 171 having two ends 173 and 175, with a portion of the bladder 171 proximal end 173 having a smaller radius to define a circumferential channel 177 for positioning a patient's thumb and index finger around channel 177 in a generally opposed relationship. In general, the inflatable bladder hand piece 142 may be used in order to straighten a patient's contracted fingers. As shown in FIG. 9, the bladder hand piece 142 is preferably wrapped within a soft fabric covering 179 that may be inserted in a deflated condition into the palmar side of a patient's hand with the patient's thumb and index finger being positioned generally around channel 177 in an opposed relationship and the forearm support attached to the patient's forearm, such as with a pair of straps 201 and 203. Preferably, straps 201 and 203 may be wrapped around the top portion of the patient's forearm 194 and be secured around the forearm 194 by a pair of mating fasteners, such as respective hook and loop fasteners 207 and 209 and also 211 and 213. In addition, fabric covering 179 preferably includes a strap 181 also having a conventional fastening means such as hook and loop fasteners 183 and 185 in order to maintain the position of the inflatable bladder 171 in the palmar portion of the patient's hand 192. The bladder 171 is inflated at valve 175, suitably by a conventional air pump (not shown), thereby straightening the contracted fingers according to the size of the bladder 171.

Another preferred hand piece is resting platform 242 shown in FIGS. 6 and 10, in which similar reference numbers, increased by adding 200, refer to similar elements as described with respect to L-shaped support 42 and connector member 34. Resting platform 242 is particularly useful as an antispasticity support for keeping a patient's hand in a generally straightened position while keeping the wrist from flexing. In general resting platform 242 includes a generally rigid, inelastically deformable planar member 245 dimensioned and configured for receiving a patient's hand and having a thumb platform 247 extending therefrom and located proximal platform first end 260. Preferably, planar member 245 has a pair of opposed side edges 249 and 251 extending between first end 260 and second end 262, with side edges 249 and 251 having a pair of opposed recessed portions creating areas of reduced width. By forming planar platform 245 of an appropriate inelastically deformable material, such as an aluminum or stainless steel sheet, the reduced width portions facilitate the bending of resting platform at positions between the recessed side edges. Accordingly, platform 242 may conveniently be adjusted to a preselected position for each patient. As shown in the preferred embodiment of FIGS. 6 and 10, the planar member 245 is covered with a foam enclosure 255, suitably VOLARA™, which conveniently may be inserted into a generally soft body fabric wrap 257 for use with the patient. The wrap 257 may include a hand strap 259 and a thumb strap 261 with each respective strap including a pair of mating fasteners, suitably hook and loop fasteners 263, 265, 267 and 269, for maintaining the engagement between the patients hand and platform 242.

Figure 5:
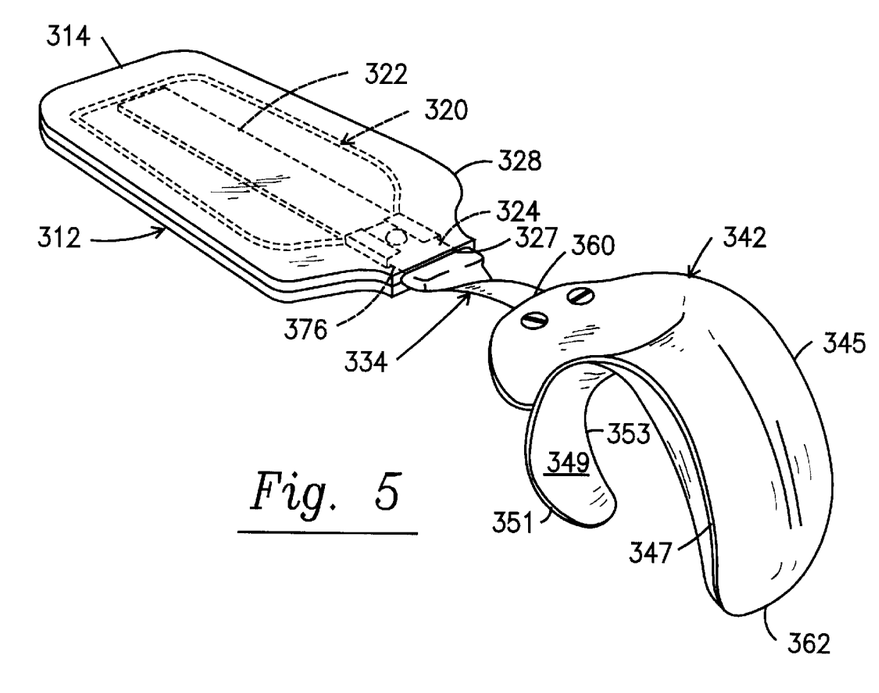
FIG. 5 is an alternative preferred embodiment of a hand splint apparatus in accordance with the present invention, illustrating a C-shaped hand piece.
Figure 6:
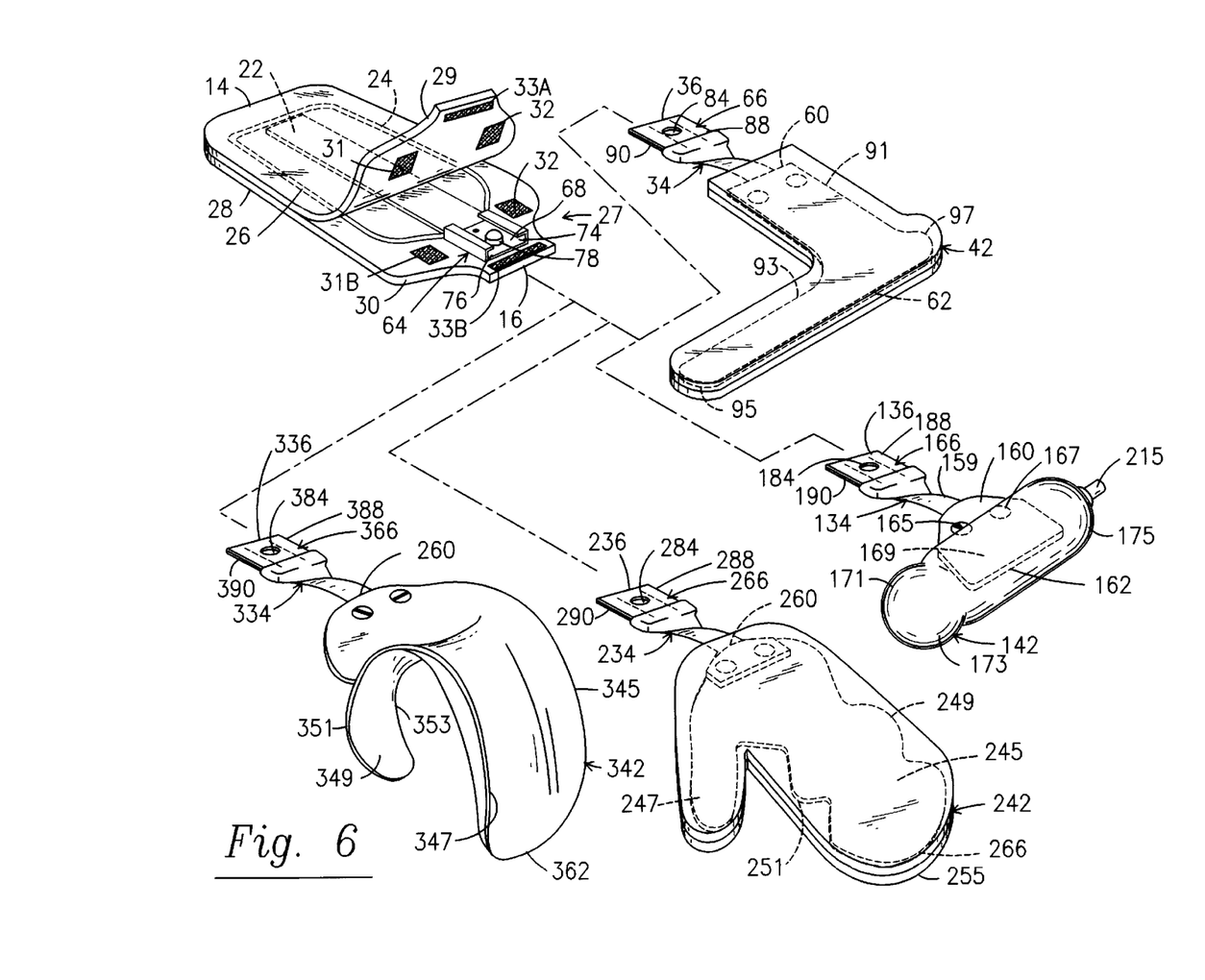
FIG. 6 is an exploded view of the hand splint apparatus of this invention with several preferred embodiments of hand pieces that may be attached to a preferred forearm support.
Figures 7, 8:
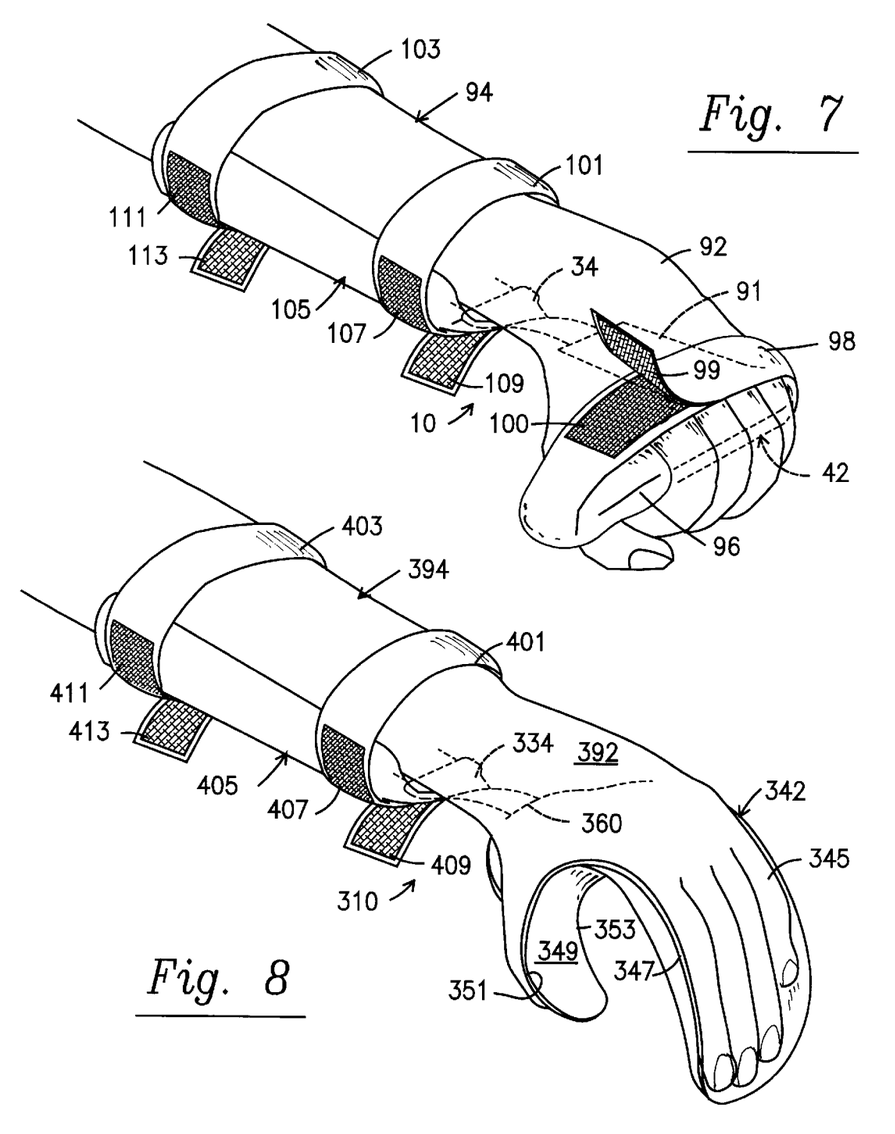
FIG. 7 is a preferred embodiment of the hand splint of FIG. 1 illustrating a preferred manner of attachment to a patient's hand and forearm.
FIG. 8 is a preferred embodiment of the hand splint of FIG. 5, illustrating a preferred manner of attachment to a patient's hand and forearm.

A fourth preferred embodiment of a hand piece illustrated in FIGS. 5, 6 and 8 as a functional C-shaped hand piece, generally indicated as 342, which is used to position a patient's thumb and index finger in a generally opposed C-shaped position. Similar reference numbers, increased by adding 300, refer to parallel elements as described with respect to L-shaped support 42 and connector member 34 described above. In general the functional C-shaped hand piece 342 prevents the thumb and the fingers from flexing while orienting the index finger in a generally opposed relationship to the thumb. Hand piece 342 has a first end 360, a second end 362, with a pair of arcuate side edges 345 and 347 extending between ends 360 and 362 that form side wall portions for holding a patient's hand in a desired position therebetween. Support 342 also includes a thumb rest that extends in generally opposed and curved relation to side edge 347 for positioning a patient's thumb opposed to and spaced apart from the corresponding index finger. In order to maintain the thumb in the appropriate opposed relationship to the patient's index finger, the thumb portion of support 342 further includes a pair of arcuate side edges 351 and 353 for engaging the side portions of a patient's thumb, thereby maintaining the thumb therebetween. As with each of the hand pieces 42, 142, and 242 described above, the functional C-shaped hand piece may be manufactured in various sizes as well as may be configured for the left or right hand. The particularly preferred embodiment illustrated in FIGS. 5, 6 and 8 is a left-hand functional opponens. The functional C-shaped hand piece 342 may be formed of a generally rigid material, such as a thermoplastic material, suitably KYDEM™, and is preferably molded or configured a according to the dimensions of a patient's hand.

With preferred embodiments of the hand splint apparatus described above, preferred methods for attaching and orienting adjustable and modular hand splints, such as those described above, to a patient's forearm and hand will now be described with respect to FIGS. 7–10. For example, when a therapist wishes to inhibit a wrist from flexing, but still allow the hand to bend, such as may be the case for a wrist contracture without severe contracture of the hand and fingers, the L-shaped hand piece 42, as shown in FIGS. 1 and 7, may be appropriate. In the situation of a severely contracted hand, the splint having an inflatable bladder hand piece 142 may be used to open the patient's hand. Where a patient is experiencing spasticity of the hand and fingers, such as is common with stroke patients, the resting platform hand piece 242 may be desirable. The functional C-shaped hand piece 342 is particularly useful to reduce and inhibit contractures of the wrist or fingers, which may accompany certain neurological conditions with muscle weakness. In addition, finger separators may also be used with each of the hand pieces in order to reduce sores that might develop due to the engagement between adjacent fingers.

Prior to applying any hand splint, such as those described above, a therapist should evaluate and assesses the amount and degree of contracture between the patient's hand and forearm 94. For the example where one selects the L-shaped support shown in FIGS. 1 and 7, the therapist appropriately adjusts one end 38 of the deformable connector 34 with respect to the other connector end 36 according to the contracture assessed by the therapist, such as by displacing end portion 56 a predetermined distance generally transverse the first plane 46 (direction A) and then displacing end 56 a predetermined distance generally parallel to first plane 46 (direction B). The transverse and parallel adjustability of connector end 50 enables the therapist to position the hand piece 42 with respect to the forearm support 12 at a position that substantially conforms to the position and orientation of the patient's hand 92 with respect to the patient's forearm 94. In order to accommodate angular radial or ulnar deviation of a patient's hand, the distal end 36 of the deformable connector 34 also may be angularly adjusted a predetermined angle about connector axis 40 (direction C) prior to urging the hand piece into engagement with the patient's hand. Once the hand splint 10 is appropriately adjusted, hand piece 42 is urged into engagement with the palmar side of the patient's hand as shown in FIG. 7.

Preferably, a soft fabric housing 96 encloses at least a substantial portion of hand piece 42 (FIG. 7) in order to provide additional comfort to the patient's hand. In order to maintain the engagement between the palmar side of the patient's hand 92 and the hand piece 42, housing 96 preferably includes a strap 98 for attaching the fabric housing 96 to the patient's hand. In order to secure the hand piece 42 within housing 96 to the patient's hand 92, strap 98 preferably includes a fastener, such as mating hook and loop fastening materials 99 and 100, attached thereto. Once the hand piece 42 is in position, the forearm support 12 is urged into engagement with the patient's forearm 94 with a pair of straps 101 and 103 attaching the forearm support 12 to the patient's forearm for a predetermined period of time, as prescribed by a physician or therapist. Straps 101 and 103 are preferably attached to a soft fabric housing or wrap 105 that encloses at least a substantial portion of forearm support 12. Wrap 105 is suitably constructed of the same material as wrap 96 that surrounds hand piece 42. Straps 101 and 103 may conveniently be wrapped around the top side of the patient's forearm 92 to maintain engagement between forearm support 12 and the patient's forearm 94 by conventional fasteners, which conveniently may be in the form of a hook and loop material, a belt and buckle combination, as well as other fasteners known to those skilled in the art. The preferred embodiment of using such fasteners include securing a hook or loop fastener 109 and 113 proximal one end of strap 101 and 103, respectively with a corresponding hook or loop fastener 107 and 111 near the other end of the respective straps 101 and 103. Thus, by wrapping the straps around the forearm and securing fasteners 107 and 109 as well as fastener 111 and 113, forearm support 12 is easily attached to the patient's forearm 94. Splints having other hand pieces, such as 142, 242 and 342, conveniently may be utilized in a substantially identical manner. They may be attached to a forearm support, be adjusted along directions A, B and C, engage the patients hand according to the configuration of the respective hand piece, with the forearm support be attached to the patient's forearm for a desired therapy period.

As shown in FIGS. 7–10, a treatment regimen may also include utilizing various combinations of different hand pieces with each hand piece 42, 142, 242 and 342 having a coupling second part 66, 166, 266 and 366, respectively, that may be removably connected to coupling 64 of the same or a different forearm support 12. In such a situation, the therapist or physician assesses a first amount of contracture between the patient's hand and forearm and the position of the hand with respect to the forearm. Based upon such contracture, the therapist selects a first hand piece 42, 142, 242 or 342 according to this first amount of contracture and to the position of the patient's hand with respect to the forearm as well as according to the therapeutic goals for that patient. The selected hand piece 42, 142, 242 or 342 is removably attached to the coupling first part 64 at the second connector end 38 of forearm support 12 to form a first hand splint, as shown in FIGS. 7–10. The hand piece 42, 142, 242 or 342 may also be adjusted with respect to the forearm support prior to attaching the respective splint 10, 110, 210 or 310 to the patient's forearm. As stated herein, such adjustment is easily accomplished by displacing or moving one of the connector parts 36 or 38 with respect to the other connector part 38 or 36 generally transverse to the first plane 46 (direction A) as well as generally parallel to the first plane 46 (direction B) according to the assessment of the second contracture and the position of the patient's hand with respect to the forearm. In addition, the angular positioning of hand piece 42, 142, 242 or 342 may be adjusted angularly about connector axis 40, 140, 240 or 340 by angular rotation of such hand piece with respect to the forearm support 12 along direction C. In this manner, the positioning of the hand piece with respect to the forearm support may be adjusted to conform substantially to the position of the patient's hand with respect to the patient's forearm. Next, as described above with respect to FIG. 7, the first selected hand piece 42, 142, 242 or 342 is then urged into engagement with the palmar portion of the patient's hand 92, 192, 292 or 392. The forearm support then is attached appropriately to the patient's forearm 94, 194, 294 or 394 to maintain the patient's hand at a first predetermined position according to the configuration of the respective hand splint 10, 110, 210 or 310. After the hand undergoes an appropriate amount of therapy for a predetermined period of time, the first hand splint may be removed from the patient by reversing the steps just described. The injury then may be reevaluated to determine a second position of the patient's hand with respect to the patient's forearm as well as a second amount of contracture between the patient's hand and forearm and, if indicated, the position of the hand piece may be adjusted by bending the connector 34 to an appropriate new position. In the event that the patient's condition may have changed, the first hand piece may be removed from the forearm support 12 and an alternative second hand piece, such as 42, 142, 242, 342, or the like, may be selected according to the position of the patient's hand and fingers as well as to the second amount of contracture. The second hand piece is then appropriately attached to the forearm support 12 by inserting coupling 66, 166, 266 or 366 into the receiving member 64 of forearm support 12 to form a second hand splint. The hand piece may then be adjusted with respect to the forearm support in a substantially identical manner as stated above, suitably displaced in directions A, B and C according to the second position of the hand with respect to the forearm and the amount of contracture. Next, the second hand piece of the second hand splint may be urged into engagement with the palmar side of the patient's hand 92, 192, 292 or 392. With the hand piece appropriately in place, the forearm support 12, preferably enclosed within a soft fabric covering 105, 205, 305 or 405, may be urged into engagement with the patient's forearm 94, 194, 294 or 394 and be attached thereto, suitably by fastening straps 101 and 103, 101 and 203, 301 and 303, or 401 and 403, in order to maintain the palmar side of the patient's hand at a second predetermined position based upon the configuration of the second hand splint 10, 110, 210 or 310 for a second predetermined period of time, suitably as dictated by the therapist or treating physician.

An appropriate combination of hand pieces may be used, for example, with a post-stroke patient experiencing contractures of the hand and wrist. In this situation, one may first utilize the resting platform hand piece 242, which generally provides an anti-spasticity position. Once the patient's spasticity ceases, the resting platform may be replaced with the functional C-shaped hand piece 342, the L-shaped bar hand piece 42 or even the inflatable bladder hand piece 142, which hand pieces all position the fingers in a typical relaxed position allowing them to curl, rather than the substantially full extension provided by the resting platform 242.

A patient experiencing severe contractures of the fingers might undergo a therapeutic regimen beginning with the inflatable bladder hand piece 142, such that the therapist can efficiently separate the fingers from the palmar portion of the patient's hand. After there is an adequate amount of separation between the fingers and the palmer region of the patient's hand, the functional C hand piece 342 may then be used. It will be understood and appreciated by those skilled in the art that numerous other hand pieces and combinations may be utilized as part of therapy for a given patient.

Numerous variations and modifications of the present invention, all within the scope of this invention, will readily occur to those skilled in the art. Such modifications may include without limitation utilizing different configurations of hand pieces, hand splints of varying dimensions and materials, among other variations. All such modifications and variations are considered to be fully within the scope of this invention. Accordingly, the foregoing detailed description is to be considered illustrative only of the principles of this invention and not to be limitative thereof. The scope of the invention is to be determined solely by the claims appended hereto.

What is claimed is:

1. An adjustable hand splint comprising:

a generally rigid forearm support having a first end, a second end, and an axis extending through said first and second ends;

an elongated and inelastically deformable connector having a first end portion defining a first plane, a second end portion and an axis extending therebetween, said connector first end attached to said forearm support at a position proximal said forearm support second end, with said connector second end distal said forearm support;

a hand piece having a first end and a second end, said connector second end portion attached to said hand piece at a position proximal said hand piece first end, with said connector second end portion being adjustable relative to said connector first end portion in a first direction generally transverse to said first plane and in a second direction generally parallel to said first plan for orienting said hand piece to a desired position with respect to said forearm support.

2. A splint according to claim 1, wherein said connector is angularly adjustable about said connector axis for adjusting the angular position of said portion with respect to said portion, whereby the hand piece may be positioned to a desired angular position with respect to the forearm support.

3. A splint according to claim 2 wherein said connector first end further comprises a generally planar member in a first plane, with said connector second end being adjustable with respect to said connector first end portion in a first direction generally transverse to said first plane and in a second direction generally parallel to said first plane.

4. A splint according to claim 1, wherein said connector further comprises a generally elongated, inelastically deformable member having first and second ends and an axis extending between said first and second member ends, said member first end being rotated about 180 degrees about said member axis with respect to said member second end to define a twist in said member, said member first end attached to said forearm support at a position proximal said forearm support second end, and said member second end attached to said hand piece at a position proximal said hand piece first end, with said member being adjustable in a plurality of directions generally transverse to said member axis for adjusting the orientation of the hand piece with respect to said forearm support.

5. A splint according to claim 4 wherein said connector deformable member further comprises:

an intermediate portion positioned between said member first and second ends having a first predetermined width, and a second portion proximal and including said member second end having a width greater than said first predetermined width of said member intermediate portion.

6. A splint according to claim 4 wherein said connector deformable member further comprises a generally rigid, inelastically deformable material requiring about 30 to about 45 pounds of force applied at one of said member ends to adjust said member in said plurality of directions.

7. A splint according to claim 1 wherein said hand splint further comprises:

a detachable coupling interposed between said hand piece first end and said forearm support second end for selectively detaching said hand piece from said forearm support and for selectively attaching said hand piece to said forearm support.

8. A splint according to claim 7, wherein said coupling further comprises:

a detent attached to said connector at a position proximal said connector first end portion, a receptacle formed in said forearm support at a position promixal to said forearm support second end, such that said detent engages said receptacle for detachably connecting said connector to said forearm support.

9. A splint according to claim 7, wherein said coupling further comprises:

a detent attached to said forearm support at a position proximal said forearm support second end;

a receptacle formed in said connector at a position proximal said connector first end portion for receiving said detent, such that said detent engages said receptacle for detachably connecting said connector to said forearm support.

10. A splint according to claim 9, wherein said coupling further comprises a female member having a pair of side edges proximal said forearm support second end, said detent positioned between said female member side edges, with said female member being configured for mating attachment to said connector first end portion.

11. A splint according to claim 7, wherein said coupling further comprises a connector receiving member comprising a receiving platform having first and second side edges spaced a predetermined distance apart and a surface extending between said side edges, said platform attached to said forearm support at a position adjacent said forearm support second end;

a pair of channels formed in said platform respective first and second side edges in a generally opposed and parallel relationship, with said pair of channels being generally parallel to said forearm support axis;

a detent positioned intermediate said pair of channels proximal said forearm support second end and extending a predetermined distance outwardly from said platform; and said connector first end portion further comprising a generally planar member dimensioned and configured for mating reception within said connector receiving member between said channels, said planar member having a receptacle formed therein for receiving said detent.

12. A splint according to claim 7 wherein said coupling further comprises:

a sleeve attached to said forearm support adjacent said forearm support second end having a pair of generally opposed and spaced apart flange members for receiving said connector first end portion, said sleeve having a detent positioned intermediate said flange members;

said connector first end portion dimensioned and configured for mating reception between said flange members, said connector having a receptacle formed therein proximal said connector first end portion for receiving said detent to removably attach said hand piece to said forearm support.

13. A splint according to claim 1, wherein said connector comprises an inelastically deformable joint positioned intermediate said connector first end portion and said connector second end portion for orienting said hand piece with respect to said forearm support to at least one of a plurality of generally fixed positions.

14. A splint according to claim 1 wherein said connector further comprises a generally rigid, inelastically deformable material being bendable in said plurality of orthogonal directions upon applying about 30 to about 40 pounds of force at one of said connector end portions.

15. A splint according to claim 1 wherein said forearm support further comprises:
   a generally rigid frame having a first end spaced apart from a second end, said frame second end attached to said connector first end portion; and
   a generally rigid elongated rib attached between said generally rigid frame first and second ends.

16. A splint according to claim 15 wherein said forearm support further comprises a foam enclosure surrounding at least a portion of said forearm support, with a portion of said enclosure at a position proximal said forearm support second end having an opening formed therein, through which said opening said connector extends.

17. A modular hand splint comprising:
   a forearm support having a first end spaced a predetermined distance from a second end, with a longitudinal axis extending between said first and second ends;
   a hand piece having first and second ends;
   a detachable connector having a first part and a mating second part,
      one of said connector parts secured to one of said forearm support second end and the other of said connector parts secured to said hand piece first end, said connector first part having a detent, said connector second part having a receptacle for engaging said detent to lock said connector second part removably to said connector first part, thereby attaching said forearm support to said hand piece, and
      one of said first and second connector parts further comprising an inelastically deformable member having an axis generally parallel to said forearm axis, with said one part of said connector being adjustable in a plurality of mutually orthogonal directions transverse to said deformable member axis for orienting said hand piece to a desired position with respect to said forearm support.

18. A hand splint according to claim 17 wherein said deformable member further comprises an inelastically deformable member angularly adjustable about said deformable member axis.

19. A splint according to claim 17 wherein:
   said connector first part further comprises a receiving member having a pair of generally parallel, spaced apart and opposed flanges, each of said flanges being generally parallel to said forearm support axis;
   said detent is formed in said receiving member of said connector first part intermediate said pair of flanges; and
   said connector second part further comprises a generally flat arm for mating attachment to said receiving member between said pair of flanges, said arm having a receptacle formed therein for receiving said detent to demountably attach said hand piece to said forearm support.

20. A method for attaching and orienting an adjustable hand splint to a patient's forearm and to a palmer side of said patient's hand, said hand splint comprising a generally rigid forearm support having a first end, a second end and a connector axis extending therebetween, said hand splint further comprising a hand piece and an elongated, inelastically deformable connector attached between said forearm support and said hand piece, said connector having two ends, one of said connector ends positioned distal said forearm support the other of said connector ends positioned proximal said forearm support and having a planar member defining a first plane, said method comprising the steps of:
   assessing the position of the patient's hand with respect to the patient's forearm;
   adjusting one end of said deformable connector with respect to the other end of said connector a predetermined distance generally transverse to said first plane and a predetermined distance generally parallel to said first plane according to the position of the patient's hand, such that the position of said hand piece with respect to said forearm support substantially conforms to the position and orientation of the patient's hand with respect to said patient's forearm;
   urging said hand piece into engagement with the palmer side of the patient's hand;
   urging said forearm support into engagement with the patient's forearm; and
   attaching said forearm support to said patient's forearm for a predetermined time period.

21. The method of claim 20 further comprising the step of angularly adjusting said distal end of said deformable connector a predetermined angle generally about said connector axis according to the position of the patient's hand.

22. The method of claim 20 wherein said step of adjusting further comprises:
   displacing said one end of said deformable connector a predetermined distance with respect to said other end of said deformable connector generally parallel to said first plane according to the position of the patient's hand, and
   displacing said one end of said deformable connector a predetermined distance with respect to said other end of said deformable connector generally transverse to said first plane according to the position of said patient's hand.

23. A method for supporting a patient's wrist, hand and/or fingers with a modular hand splint comprising a forearm support having first and second ends, an axis extending between said first and second ends, and a generally planar surface for engaging the patient's forearm, said planar surface defining a first plane, a connector second part attached to said forearm support second end and a plurality of hand pieces, each of said hand pieces having a connector first part attached thereto, with each said connector first part being removably attachable to said connector second part, said method comprising the steps of:
   assessing a first position of a patient's hand and fingers;
   selecting a first said hand piece having a connector first part attached thereto, with said first hand piece having dimensions and a configuration generally conforming to said first position of the patient's hand and fingers;
   removably attaching said connector first part of said first hand piece to said connector second part of said forearm support to form a first hand splint;
   urging said first hand piece of said first hand splint into engagement with a palmer portion of the patient's hand;
   attaching said forearm support of said first hand splint to the patient's forearm, thereby maintaining at least a portion of the patient's hand at a first predetermined position according to said configuration of said first hand splint for a first predetermined period of time;

removing said first hand splint from the patient after said first predetermined period of time;

assessing a second position of the patient's hand and fingers;

detaching said first hand piece from said forearm support;

selecting a second said hand piece having a connector first part, said second hand piece having dimensions and a configuration generally conforming to said second position of the patient's hand and fingers;

removably attaching a first connector part of said second hand piece to said connector second part of said forearm support to form a second hand splint;

urging said second hand piece of said second hand splint into engagement with said palmer side of the patient's hand; and attaching said forearm support of said second splint to the patient's forearm, thereby maintaining said palmer side of the patient's hand at a predetermined position based upon the configuration said second hand splint for second a predetermined period of time.

24. A method according to claim 23 wherein said connector further comprises a generally rigid, elastically deformable member positioned between said first and second parts of said connector and a deformable member axis extending through said connector first and second parts, said method further comprising the step of:

prior to said step of urging said first hand piece, displacing one of said connector parts with respect to the other of said connector parts a predetermined distance generally transverse to said connector axis and a predetermined distance generally parallel to said first plane according to the position of said patient's hand with respect to said patient's forearm, such that the positioning of said hand piece with respect to said forearm support substantially conforms to the positioning of said patient's hand with respect to said patient's forearm.

* * * * *

UNITED STATES PATENT AND TRADEMARK OFFICE
CERTIFICATE OF CORRECTION

PATENT NO. : 5,916,186
DATED : June 29, 1999
INVENTOR(S) : Craig H. Turtzo, et al It is certified that error appears in the above-indentified patent and that said Letters Patent is hereby corrected as shown below:

On the title page of the patent, in the header please correct the inventor designation to read "Turtzo, et al." and in the Inventor item 75 please correct the surname of the first named inventor to read "Turtzo".

IN THE CLAIMS

In column 11, line 25, replace "plan" with --plane--;

In column 11, line 30 after the first occurrence of "said" insert --connector second end-- and after the second occurrence of "said" insert --connector first end--;

In column 11, line 34 after "end" insert --portion--;

In column 11, line 35 after "end" insert --portion--;

Signed and Sealed this

Fourth Day of January, 2000

Attest:

Attesting Officer

*Acting Commissioner of Patents and Trademarks*